(12) United States Patent
Tanimoto et al.

(10) Patent No.: US 6,664,416 B2
(45) Date of Patent: Dec. 16, 2003

(54) PROCESS FOR PRODUCING (METH) ACRYLIC ACID

(75) Inventors: Michio Tanimoto, Himeji (JP); Hiroto Kasuga, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/118,112

(22) Filed: Apr. 6, 2002

(65) Prior Publication Data

US 2002/0193632 A1 Dec. 19, 2002

(30) Foreign Application Priority Data

Apr. 25, 2001 (JP) ........................................ 2001-128336

(51) Int. Cl.⁷ ........................ C07C 51/235; C07C 51/16; C07C 51/10
(52) U.S. Cl. ........................ 562/532; 562/542; 562/545; 562/518; 562/531
(58) Field of Search ................................. 562/532, 545, 562/518, 531, 542

(56) References Cited

U.S. PATENT DOCUMENTS

| | | | | |
|---|---|---|---|---|
| 3,567,772 A | * | 3/1971 | Yanagita et al. | 562/534 |
| 3,567,773 A | * | 3/1971 | Yamaguchi et al. | 562/535 |
| 3,775,474 A | * | 11/1973 | Ohara et al. | 562/535 |
| 3,799,978 A | * | 3/1974 | Ohara et al. | 562/546 |
| 3,893,951 A | * | 7/1975 | Grasselli et al. | 502/307 |
| 3,954,855 A | * | 5/1976 | Wada et al. | 502/178 |
| 4,339,355 A | * | 7/1982 | Decker et al. | 502/343 |

FOREIGN PATENT DOCUMENTS

| | | |
|---|---|---|
| EP | 0 608 838 A2 | 8/1994 |
| EP | 0 711 745 A1 | 5/1996 |
| EP | 1 055 455 A2 | 11/2000 |
| GB | 1 438 806 | 6/1976 |
| JP | 7-10801 A | 1/1995 |
| JP | 8-206504 A | 8/1996 |
| JP | 2000-325795 A | 11/2000 |
| JP | 2001-342169 A | 12/2001 |
| WO | WO 01/21570 A1 | 3/2001 |

* cited by examiner

Primary Examiner—Alan L. Rotman
Assistant Examiner—Taylor V. Oh
(74) Attorney, Agent, or Firm—Haugen Law Firm PLLP

(57) ABSTRACT

The present invention produces (meth)acrylic acid in a high yield in a process for producing (meth)acrylic acid by subjecting at least one member selected from the group consisting of (meth)acrolein, propane, and isobutane to catalytic gas phase oxidation with molecular oxygen or a molecular-oxygen-containing gas. In addition, the present invention makes it possible to produce (meth)acrylic acid in a high yield and stably for a long time. The present invention provides a process for producing (meth)acrylic acid by catalytic gas phase oxidation reaction, which is characterized by allowing a reaction gas to contain a reducible compound.

5 Claims, 2 Drawing Sheets

Catalyst as treated with $SO_2$-free reaction gas

Catalyst as treated with $SO_2$-added reaction gas

Infrared-spectroscopically analytic chart

PROCESS FOR PRODUCING (METH)ACRYLIC ACID

BACKGROUND OF THE INVENTION

A. Technical Field

The present invention relates to a process for producing (meth)acrylic acid by catalytic gas phase oxidation reaction. Specifically, the invention relates to a process for producing (meth)acrylic acid stably for a long time by allowing a reaction gas to contain a reducible compound when subjecting at least one member selected from the group consisting of (meth)acrolein, propane, and isobutane to the catalytic gas phase oxidation with a molecular-oxygen-containing gas. More specifically, the invention relates to a process for producing (meth)acrylic acid stably for a long time by stabilizing a catalyst (containing molybdenum and vanadium as essential components) by allowing a reaction gas to contain a reducible compound.

B. Background Art (Meth)acrylic acid are industrially important as raw materials for such as various synthetic resins, paints and plasticizers. Known as the most common process for producing (meth)acrylic acid is a process which comprises the steps of subjecting propylene and isobutene to catalytic gas phase oxidation to produce (meth)acrolein and further subjecting this (meth)acrolein to catalytic gas phase oxidation to produce (meth)acrylic acid. Also known is a process in which (meth)acrylic acid are produced by one step using propane and isobutane (which are cheaper) as starting materials.

However, as to the hitherto known processes, the yield of (meth)acrylic acid is not sufficiently high, and further there are cases where the yield decreases if (meth)acrylic acid are produced for a long time.

SUMMARY OF THE INVENTION

A. Objects of the Invention

An object of the present invention is to provide a process for producing (meth)acrylic acid by which (meth)acrylic acid can be produced in a high yield in a process for producing (meth)acrylic acid by subjecting at least one member selected from the group consisting of (meth)acrolein, propane, and isobutane to catalytic gas phase oxidation with molecular oxygen or a molecular-oxygen-containing gas.

Another object of the present invention is to provide a novel process for producing (meth)acrylic acid which makes it possible to produce (meth)acrylic acid in a high yield and stably for a long time in a process for producing (meth)acrylic acid by subjecting at least one member selected from the group consisting of (meth)acrolein, propane, and isobutane to catalytic gas phase oxidation with molecular oxygen or a molecular-oxygen-containing gas.

B. Disclosure of the Invention

To solve the above problems, a process for producing (meth)acrylic acid, according to the present invention, is a process for producing (meth)acrylic acid by catalytic gas phase oxidation reaction, and is characterized by allowing a reaction gas to contain a reducible compound.

These and other objects and the advantages of the present invention will be more fully apparent from the following detailed disclosure.

DETAILED DESCRIPTION OF THE INVENTION

Figure 1:
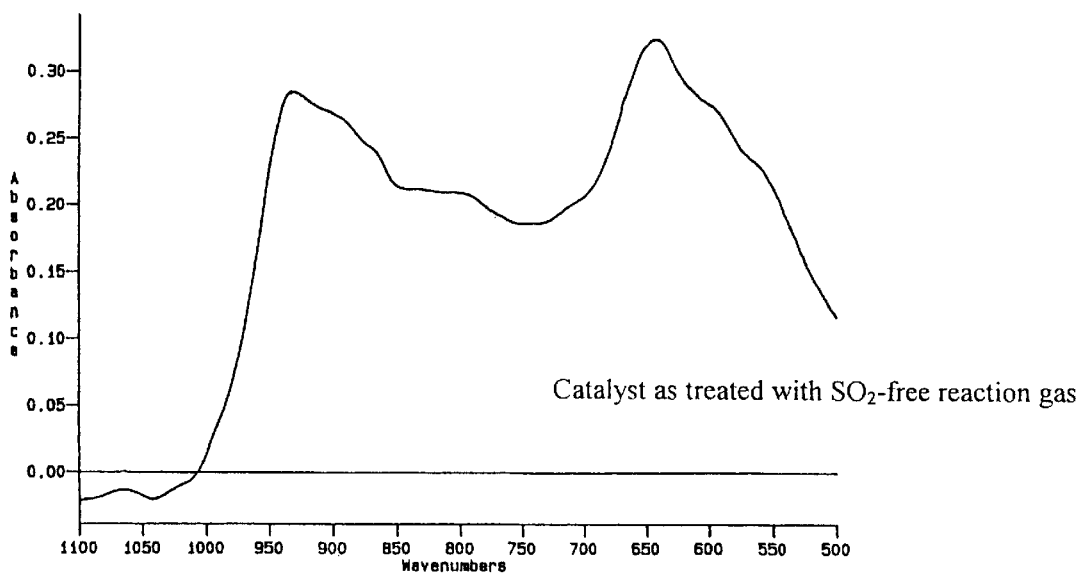
FIG. 1 shows the results of analysis by infrared spectrophotometry (KBr method) with regard to a catalyst as treated without sulfur dioxide added.

Examples of materials usable as raw reaction materials in the present invention process for producing (meth)acrylic acid include at least one member selected from the group consisting of (meth)acrolein, propane, and isobutane. In other words, the following four kinds of reactions are included. In the present invention, at least two of these four kinds of reactions may be carried out simultaneously.

(1) Oxidation of acrolein, thereby producing acrylic acid.

(2) Oxidation of propane, thereby producing acrylic acid.

(3) Oxidation of methacrolein, thereby producing methacrylic acid.

(4) Oxidation of isobutane, thereby producing methacrylic acid.

Examples of materials favorably usable as acrolein in (1) above include such as produced by subjecting propylene to catalytic gas phase oxidation with molecular oxygen or a molecular-oxygen-containing gas in the presence of a catalyst containing molybdenum, bismuth, and iron as essential components.

Similarly, examples of materials favorably usable as methacrolein in (3) above include such as produced by subjecting isobutylene to catalytic gas phase oxidation with molecular oxygen or a molecular-oxygen-containing gas in the presence of a catalyst containing molybdenum, bismuth, and iron as essential components.

In (2) and (4) above, it is also possible that propane and isobutane are mixed with propylene (raw material to produce acrolein) and isobutylene (raw material to produce methacrolein) respectively and then used.

The commonly known two-step oxidation reaction is a process which comprises: the first step of subjecting propylene and/or isobutylene to catalytic gas phase oxidation in the presence of a molybdenum-bismuth-iron oxide catalyst, thereby producing (meth)acrolein and (meth)acrylic acid (mainly, (meth)acrolein); and the second step of subjecting the resultant reaction gas to catalytic gas phase oxidation in the presence of a molybdenum-vanadium oxide catalyst, thereby producing (meth)acrylic acid.

In the present invention, furthermore, it is also possible to use a mixture of propylene and propane and/or a mixture of isobutylene and isobutane as raw materials in the above two-step oxidation reaction.

The reaction mode of the catalytic gas phase oxidation reaction in the present invention is not especially limited, and the reaction can be carried out using any of fluidized beds, moving beds, and fixed beds.

The present invention is characterized by allowing a reaction gas to contain a reducible compound in the catalytic gas phase oxidation reaction. Examples of materials usable as the reducible compound include compounds commonly known as reducing agents, such as sulfur-containing compounds and organic compounds (e.g. formic acid and oxalic acid), but the sulfur-containing compounds are favorable. Examples of the sulfur-containing compounds include sulfur dioxide and hydrogen sulfide, but sulfur dioxide is particularly favorable.

In the case of the above two-step manner including the step of oxidizing propylene and/or isobutylene, examples of methods for introducing the reducible compound include the following two methods: (1) a method in which the reducible compound is added to a raw material gas being introduced into the first step; and (2) a method in which the reducible compound is added to a reaction gas being introduced into the second step. In the case of the latter, the reducible compound can be mixed with such as oxygen and/or water vapor and then added to the reaction gas being introduced into the second step, wherein the oxygen means a component which contains molecular oxygen, and examples thereof include pure oxygen and air. The reducible compound can be added to the reaction gas either throughout continuously or intermittently.

The amount of the reducible compound added is favorably not smaller than 1 ppm, more favorably in the range of 10 to 5,000 ppm, still more favorably in the range of 30 to 3,000 ppm, on the basis of the reaction gas. In the case where the amount of the reducible compound added is small, there is obtained no improving effect on the yield of the aimed products and the life time of the catalyst. On the other hand, even if the reducible compound is added in an amount exceeding the above range, there is obtained no greatly improving effect on the yield and the life time.

In the case where the sulfur-containing compound is used as the reducible compound, the sulfur-containing compound causes such as corrosion of apparatuses in the steps of collection, absorption, and purification of the aimed products, namely, (meth)acrylic acid, therefore it is favorable that when a catalyst containing molybdenum and vanadium as essential components is packed into a reaction tube, a packed layer of solid granules containing an element to form a compound with sulfur is set on the reaction gas outlet side for the purpose of capturing the sulfur-containing compound. Usable examples of the element to form a compound with sulfur include solid granules containing an element commonly known as such, but solid granules containing an alkaline earth metal are particularly favorable for achieving the above objects. Specific examples thereof include oxides of alkaline earth metals such as magnesium oxide, calcium oxide, strontium oxide, and barium oxide.

In the present invention, although not especially limited, the catalyst used to produce (meth)acrylic acid by oxidation of at least one member selected from the group consisting of (meth)acrolein, propane, and isobutane is favorably such as contains molybdenum and vanadium as essential components, and more favorably a metal oxide shown by the following general formula (1):

$$Mo_a V_b A_c B_d C_e D_f E_g O_x \qquad (1)$$

(wherein: Mo is molybdenum; V is vanadium; A is at least one element selected from the group consisting of tungsten, antimony, niobium, and tin; B is at least one element selected from the group consisting of silicon, aluminum, titanium, and zirconium; C is at least one element selected from the group consisting of phosphorus, tellurium, cerium, lead, arsenic, boron, and zinc; D is at least one element selected from the group consisting of copper, iron, cobalt, nickel, and manganese; E is at least one element selected from the group consisting of alkaline metals and alkaline earth metals; and O is oxygen; and wherein: a, b, c, d, e, f, g, and x denote atomic ratios of Mo, V, A, B, C, D, E, and O respectively wherein: when a=12, then $0.1 \leq b \leq 15$, $0 \leq c \leq 10$, $0 \leq d \leq 10$, $0 \leq e \leq 10$, $0 \leq f \leq 10$, $0 \leq g \leq 10$; and x is a numerical value determined by the oxidation state of each element.)

Although not especially limited, examples of usable forms of the above catalyst include: those which are obtained by molding the metal oxide itself mentioned above as a catalytically active component; or those which are obtained by supporting the metal oxide (mentioned above as a catalytic component) on an inactive support. Incidentally, usable examples of the inactive support include: various oxides (e.g. alumina, silica, titania, zirconia) or their mixtures; composite oxides; and silicon carbide, silicon nitride, mullite, and steatite.

In addition, the shape of the catalyst may be any shape of such as granules, spheres, pellets, and rings.

Figure 2:
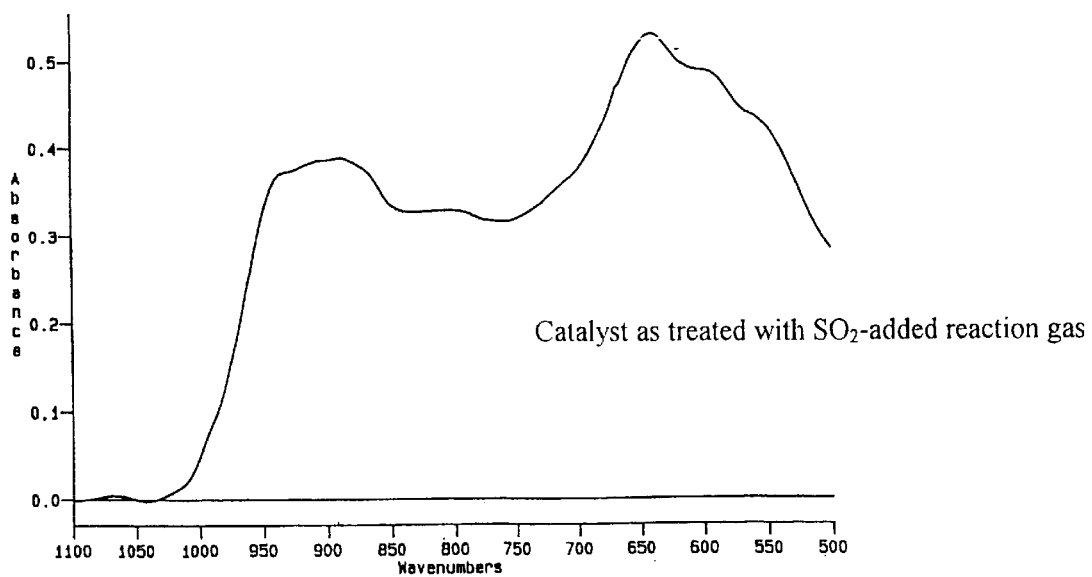
FIG. 2 shows the results of analysis by infrared spectrophotometry (KBr method) with regard to a catalyst as treated with sulfur dioxide added.
Figure 3:
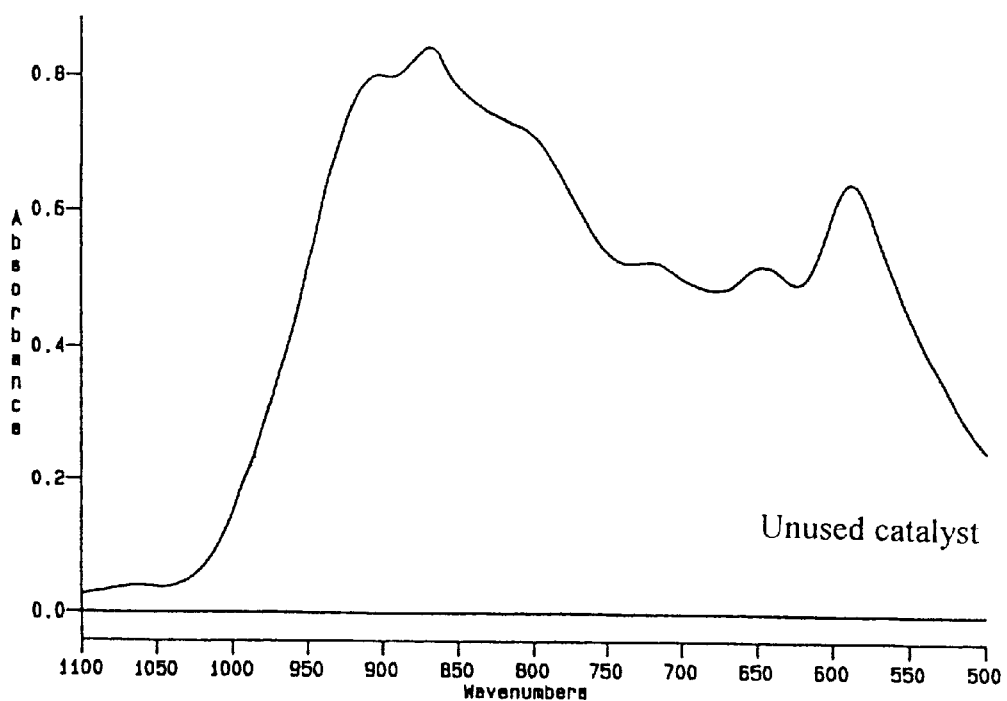
FIG. 3 shows the results of analysis by infrared spectrophotometry (KBr method) with regard to an unused catalyst.

To confirm the effects of the present invention, the present inventors made a comparative examination of a catalyst which had contacted a reaction gas containing the sulfur-containing compound and a catalyst which had contacted a reaction gas free of the sulfur-containing compound. Its specific process was as follows. A molybdenum-vanadium catalyst which had been subjected to an oxidation reaction of acrolein for 8,000 hours in the same way as of Comparative Example 1 was extracted from a reaction tube and then uniformly mixed, thus preparing two samples of 100 ml of the extracted catalyst. These samples were packed into their respective stainless U-shaped reaction tubes of 25 mm in inner diameter. Through one of the reaction tubes there was passed a flow of an acrolein-containing gas (acrolein 3 volume %, water vapor 10 volume %, air 87 volume %) at a heating medium temperature of 270° C. and a contact time of 1.8 seconds for 1 hour, and through the other reaction tube there was passed in the same way a flow of a gas which had been prepared by adding sulfur dioxide to the aforementioned acrolein-containing gas in an amount of 500 ppm on the basis of this acrolein-containing gas. In FIGS. 1 to 3 respectively there are shown the results of analysis by infrared spectrophotometry (KBr method) with regard to the following: the catalyst as treated without sulfur dioxide added; the catalyst as treated with sulfur dioxide added; and an unused catalyst.

It has been found out by adding sulfur dioxide to the reaction gas that the catalyst as treated without sulfur dioxide added shows a peak near 930 $cm^{-1}$, but that the catalyst as treated with sulfur dioxide added shows a peak near 890 $cm^{-1}$ and is therefore near to the unused catalyst which shows a peak near 870 $cm^{-1}$.

From analysis by EPMA (Electron Probe Microanalysis), it has been found out that a sulfur component is present (adsorbed) on the catalyst.

In addition, the results of the reactions with the above acrolein-containing gases showed that the addition of sulfur dioxide to the reaction gas enhanced the conversion of acrolein and the yield of acrylic acid.

From these results, it can be inferred that: as a result of the addition of the sulfur-containing compound to the reaction gas, the sulfur component is adsorbed on the catalyst to give an influence on the electronic states of the elements composing the catalyst, thereby giving some effect on the enhancement and stabilization of the catalytic performance.
(Effects and Advantages of the Invention):

The present invention makes it possible to produce (meth) acrylic acid in a high yield and stably for a long time.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to the below-mentioned examples.

In the examples and the comparative examples below, the conversion of raw material and the yield of (meth)acrylic acid were determined by the following equations respectively:

Conversion of raw material (mol %)=(molar number of reacted raw material)/(molar number of supplied raw material)×100

Yield of (meth)acrylic acid (mol %)=(molar number of formed (meth)acrylic acid)/(molar number of supplied raw material)×100

EXAMPLE 1

(Preparation of Molybdenum-bismuth-iron Catalyst):

A catalyst for oxidation of propylene was prepared by a process of Example 1 as set forth in JP-A-325795/2000. This catalyst was referred to as catalyst A.

(Preparation of Molybdenum-vanadium Catalyst):

A catalyst for oxidation of acrolein was prepared by a process of Example 1 as set forth in JP-A-206504/1996. This catalyst was referred to as catalyst B.

(Oxidation Reaction):

(1) A mixture of 50:50 in volume ratio of the catalyst A and a diluent (ceramic balls), (2) a mixture of 70:30 in volume ratio of the catalyst A and the diluent, and (3) the catalyst A were packed at packed-layer lengths of 500 mm, 500 mm, and 2,000 mm respectively in arrangement order of (1), (2), (3) along the way of from the gas inlet side to the gas outlet side of a first reactor in a reaction apparatus comprising a series of two reaction tubes of 25 mm in inner diameter and 3,500 mm in length as equipped with a jacket for heating-medium circulation wherein the reaction tubes were connected to each other's one end through piping.

(1) A mixture of 70:30 in volume ratio of the catalyst B and a diluent (ceramic balls) and (2) the catalyst B were packed at packed-layer lengths of 700 mm and 2,000 mm respectively in arrangement order of (1), (2) along the way of from the gas inlet side to the gas outlet side of a second reactor.

A mixed gas, comprising sulfur dioxide 800 ppm, propylene 9 volume %, oxygen 16 volume %, water vapor 10 volume %, and inert gas (comprising such as nitrogen) 64.92 volume %, was introduced into the first reactor at a rate of 2,200 L (Normal)/hour. The reaction was initiated at heating-medium temperatures of 310° C. for the first reactor and 260° C. for the second reactor under an outlet pressure of 0.13 MPa (absolute pressure) of the second reactor, and this reaction was continued while the respective heating-medium temperatures of the first and second reactors were adjusted so as to give a conversion of propylene of 97 mol % and a yield of acrolein of 1 mol %. The performances in the initial stage of the reaction (50 hours after the initiation of the reaction; hereafter the same) and at a passage of 8,000 hours are shown in Table 1.

COMPARATIVE EXAMPLE 1

The reaction was carried out in the same way as of Example 1 except that no sulfur dioxide was added to the reaction gas being introduced into the first reactor, and that the ratio of the inert gas (comprising such as nitrogen) was 65 volume %. The performances in the initial stage of the reaction and at a passage of 8,000 hours are shown in Table 1.

EXAMPLE 2

The reaction was carried out in the same way as of Comparative Example 1 except that sulfur dioxide was added to the reaction gas for 24 hours every reaction time of 2,000 hours, thus introducing a reaction gas comprising sulfur dioxide 2,000 ppm, propylene 9 volume %, oxygen 16 volume %, water vapor 10 volume %, and inert gas (comprising such as nitrogen) 64.8 volume %. The performances in the initial stage of the reaction and at a passage of 8,000 hours are shown in Table 1.

TABLE 1

| | Reaction time | Heating-medium temperature of second reactor (° C.) | Yield of acrylic acid (mol %) |
|---|---|---|---|
| Example 1 | Initial stage of reaction | 260 | 88.0 |
| | After 8,000 hours | 263 | 87.8 |
| Comparative Example 1 | Initial stage of reaction | 260 | 87.5 |
| | After 8.000 hours | 275 | 85.5 |
| Example 2 | Initial stage of reaction | 260 | 87.5 |
| | After 8,000 hours | 265 | 87.6 |

EXAMPLE 3

The reaction was carried out in the same way as of Comparative Example 1 except that at a passage of 8,000 hours, sulfur dioxide was added to the reaction gas being introduced into the first reactor, thereby adjusting the composition of the reaction gas to sulfur dioxide 1,000 ppm, propylene 9 volume %, oxygen 16 volume %, water vapor 10 volume %, and inert gas (comprising such as nitrogen) 64.9 volume %. The results of the performances in this process are shown in Table 2.

EXAMPLE 4

The reaction was carried out in the same way as of Example 3 except that a molding of 5 mm in diameter and 5 mm in length comprising calcium oxide was packed at a length of 300 mm on the gas outlet side of the second reactor. The results are shown in Table 2.

TABLE 2

| | Heating-medium temperature of second reactor (° C.) | Yield of acrylic acid (mol %) |
|---|---|---|
| Example 3 | 269 | 87.1 |
| Example 4 | 268 | 87.0 |

EXAMPLE 5

Each catalyst was packed in the same way as of Example 1 except that a nozzle was equipped to the piping which connected the outlet of the first reactor and the inlet of the second reactor in the reaction apparatus of Example 1.

A mixed gas, comprising propylene 10 volume %, oxygen 15 volume %, water vapor 10 volume %, and inert gas (comprising such as nitrogen) 65 volume %, was introduced into the first reactor at a rate of 2,200 L (Normal)/hour. A mixed gas, comprising air and sulfur dioxide, was added to an outlet gas of the first reactor from the above nozzle at a rate of 420 L (Normal)/hour. The reaction was initiated at heating-medium temperatures of 315° C. for the first reactor and 265° C. for the second reactor under an outlet pressure of 0.15 MPa (absolute pressure) of the second reactor. In this process, the composition of the reaction gas being introduced into the inlet of the second reactor was as follows:

| | |
|---|---|
| Sulfur dioxide | 50 ppm |
| Acrolein | 6.8 volume % |
| Propylene + carbon oxide | 1.2 volume % |
| Oxygen | 5.7 volume % |
| Water vapor | 17.8 volume % |
| Organic compounds as by-products | 1.495 volume % |
| The balance | 67.0 volume % |

The reaction was continued while the respective heating-medium temperatures of the first and second reactors were adjusted so as to give a conversion of propylene of 97 mol % and a yield of acrolein of 1 mol % in total of the first and second reactors. The performances in the initial stage of the reaction and at a passage of 8,000 hours are shown in Table 3.

COMPARATIVE EXAMPLE 2

The reaction was carried out in the same way as of Example 5 except that no sulfur dioxide was added to the reaction gas being introduced into the second reactor. The performances in the initial stage of the reaction and at a passage of 8,000 hours are shown in Table 3.

EXAMPLE 6

The reaction was still continued after a passage of 8,000 hours in Example 5. As a result, it was after a passage of 26,000 hours that the heating-medium temperature of the second reactor reached 284° C. In addition, at that time, the yield of acrylic acid was 86.3 mol %.

TABLE 3

| | Reaction time | Heating-medium temperature of second reactor (° C.) | Yield of acrylic acid (mol %) |
|---|---|---|---|
| Example 5 | Initial stage of reaction | 265 | 87.5 |
| | After 8,000 hours | 270 | 87.0 |
| Comparative Example 2 | Initial stage of reaction | 265 | 86.0 |
| | After 8,000 hours | 284 | 84.3 |

EXAMPLE 7

(Preparation of catalyst):
An Mo—V—Te—Nb catalyst was prepared by Referential Example 1 as set forth in JP-A-010801/1995. This catalyst was referred to as catalyst C.
(Oxidation reaction):
Into a reaction tube, there was packed 0.5 g of the catalyst C and then introduced a mixed gas, comprising sulfur dioxide 500 ppm, propane 5 volume %, oxygen 15 volume %, water vapor 20 volume %, and inert gas (comprising such as nitrogen) 59.95 volume %, at a reaction temperature of 400° C. and a contact time of 1.8 seconds. The results are shown in Table 4.

COMPARATIVE EXAMPLE 3

The reaction was carried out in the same way as of Example 7 except that no sulfur dioxide was added to the reaction gas, and that the ratio of the inert gas (comprising such as nitrogen) was 60 volume %. The performances are shown in Table 4.

TABLE 4

| | Conversion of propane (mol %) | Yield of acrylic acid (mol %) |
|---|---|---|
| Example 7 | 60.4 | 36.0 |
| Comparative Example 3 | 53.7 | 21.4 |

EXAMPLE 8

(Preparation of catalyst):
An amount of 1,236 g of ammonium paramolybdate and 68.2 g of ammonium metavanadate were dissolved into 2,800 ml of heated water and stirred. To the resultant solution, there were added 280 g of pyridine and 87.4 g of phosphoric acid (85 weight %), and then 400 g of nitric acid (65 weight %) and a solution as prepared by dissolving 136.4 g of cesium nitrate and 14.1 g of copper nitrate into 1,000 ml of water. The resultant mixture was concentrated by heating under stirring. Then, the resultant clayey substance was molded into the shape of a column of 5 mmφ×6 mmL, and then dried at 250° C., and then sintered at 430° C. under nitrogen gas flow for 4 hours and then at 400° C. under air flow for 2 hours, thus obtaining a catalyst D. This catalyst was $P_{1.3}Mo_{12}V_1Cu_{0.1}Cs_{1.2}$ in atomic ratio of metal elements except oxygen.

From the results of the measurement by X-ray diffraction (pairing cathode: Cu—Kα), this catalyst was found to have the composition comprising molybdovanadophosphoric acid and its partial metal salts as main components.
(Oxidation reaction):
Into a stainless U-shaped tube of 25 mm in inner diameter, there was packed 50 ml of the catalyst D and then introduced a mixed gas, comprising sulfur dioxide 200 ppm, methacrolein 3.5 volume %, oxygen 9 volume %/o, water vapor 20 volume %, and inert gas (comprising such as nitrogen) 67.48 volume %, at a contact time of 3.6 seconds with the tube immersed in a melted-salt bath of 280° C. The results are shown in Table 5.

COMPARATIVE EXAMPLE 4

The reaction was carried out in the same way as of Example 8 except that no sulfur dioxide was added, and that the ratio of the inert gas (comprising such as nitrogen) was 67.5 volume %. The results are shown in Table 5.

TABLE 5

| | Conversion of methacrolein (mol %) | Yield of methacrylic acid (mol %) |
|---|---|---|
| Example 8 | 82.0 | 67.5 |
| Comparative Example 4 | 79.6 | 63.1 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for producing (meth)acrylic acid by catalytic gas phase oxidation reaction, wherein a reaction gas is allowed to contain a sulfur-containing compound, wherein at least one member selected from the group consisting of (meth)acrolein, propane, and isobutane is subjected to the catalytic gas phase oxidation with molecular oxygen, and wherein the sulfur-containing compound is sulfur dioxide or hydrogen sulfide.

2. A process according to claim 1, wherein the catalytic gas phase oxidation is carried out in the presence of a catalyst containing molybdenum and vanadium as essential components.

3. A process according to claim 1, wherein a packed layer of solid granules containing magnesium, calcium, strontium or barium is set on the reaction gas outlet side.

4. A process according to claim 1, wherein the sulfur-containing compound is sulfur dioxide.

5. A process for producing (meth)acrylic acid by catalytic gas phase oxidation reaction, wherein a reaction gas is allowed to contain a sulfur-containing compound, wherein at least one member selected from the group consisting of (meth)acrolein, propane, and isobutane is subjected to the catalytic gas phase oxidation with a gas containing a sufficient amount of molecular oxygen for the catalytic gas phase oxidation, and wherein the sulfur-containing compound is sulfur dioxide or hydrogen sulfide.

* * * * *